United States Patent
Smith et al.

(10) Patent No.: US 12,324,692 B2
(45) Date of Patent: Jun. 10, 2025

(54) JOINT FOR A SCAN WINDOW FORMED TO A CYLINDER

(71) Applicant: GE Precision Healthcare LLC, Wauwatosa, WI (US)

(72) Inventors: Michael Eric Smith, Whitewater, WI (US); Brandon Allan Smith, Waukesha, WI (US); Wesley George Heiman, Mukwonago, WI (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 549 days.

(21) Appl. No.: 17/678,525

(22) Filed: Feb. 23, 2022

(65) Prior Publication Data

US 2023/0263484 A1 Aug. 24, 2023

(51) Int. Cl.
| | |
|---|---|
| *A61B 6/03* | (2006.01) |
| *A61B 6/00* | (2024.01) |
| *B29C 65/00* | (2006.01) |
| *G01N 23/04* | (2018.01) |
| *G01V 5/22* | (2024.01) |

(52) U.S. Cl.
CPC .............. *A61B 6/035* (2013.01); *A61B 6/032* (2013.01); *A61B 6/4435* (2013.01); *B29C 66/4324* (2013.01); *G01N 23/04* (2013.01); *G01N 2223/317* (2013.01); *G01V 5/22* (2024.01)

(58) Field of Classification Search
CPC ....... A61B 6/035; A61B 6/032; A61B 6/4435; A61B 6/44; A61B 6/4429; B29C 66/4324; G01N 23/04; G01N 2223/317; G01N 23/046; G01V 5/22
See application file for complete search history.

(56) References Cited

U.S. PATENT DOCUMENTS

| | | | |
|---|---|---|---|
| 6,704,125 B1 * | 3/2004 | Mui | G03G 15/605 358/497 |
| 11,389,126 B2 * | 7/2022 | Imaizumi | H05G 1/04 |
| 2005/0088708 A1 * | 4/2005 | Sheng | H04N 1/0405 358/487 |
| 2015/0265229 A1 * | 9/2015 | Maki | A61B 6/032 378/197 |
| 2016/0374632 A1 * | 12/2016 | David | A61B 6/4423 378/161 |
| 2020/0137861 A1 | 4/2020 | Imaizumi et al. | |

(Continued)

FOREIGN PATENT DOCUMENTS

| | | | | |
|---|---|---|---|---|
| EP | 4233727 B1 * | 8/2024 | ........... | G01N 23/046 |
| JP | 2006163377 A * | 6/2006 | ............... | G02B 5/30 |

(Continued)

OTHER PUBLICATIONS

JP application 2023-009134 filed Jan. 25, 2023—Office Action issued Jan. 31, 2024; Machine Translation; 6 pages.

(Continued)

*Primary Examiner* — David P Porta
*Assistant Examiner* — Gisselle M Gutierrez (57) ABSTRACT

A scan window for an imaging system includes at least one flexible sheet made of an X-ray transparent material and having a first end and a second end. The scan window also includes at least one tapered joint formed between the first end and the second end and secured via a bonding agent to form a joined member with the at least one flexible sheet.

17 Claims, 7 Drawing Sheets

(56) References Cited

U.S. PATENT DOCUMENTS

2020/0205752 A1* 7/2020 Zhang .................. A61B 6/102
2021/0361248 A1* 11/2021 Wang .................. A61B 6/4233

FOREIGN PATENT DOCUMENTS

JP  2011203356 A  10/2011
JP  2020069382 A  5/2020

OTHER PUBLICATIONS

JP2006163377 English Abstract; Espacenet search Jul. 18, 2024; 1 page.
JP2011203356 English Abstract; Espacenet search Jul. 18, 2024; 1 page.
JP2020069382 English Abstract; Espacenet search Jul. 18, 2024; 1 page.
Microfilm of Japanese Utility Model Application No. S48-068390 (JP S50-016176U) published Feb. 20, 1975; (Document showing well-known arts); no title available; no applicant available.

* cited by examiner

JOINT FOR A SCAN WINDOW FORMED TO A CYLINDER

BACKGROUND

The subject matter disclosed herein relates to imaging systems and, more particularly, to utilizing a joint for forming a scan window into a cylinder for utilization in an imaging system.

In computed tomography (CT), X-ray radiation spans an object or a subject of interest being scanned, such as a human patient, baggage, or other object, and a portion of the radiation impacts a detector where the image data is collected. In digital X-ray systems a photodetector produces signals representative of the amount or intensity of radiation impacting discrete pixel regions of a detector surface. The signals may then be processed to generate an image that may be displayed for review. In the images produced by such systems, it may be possible to identify and examine the internal structures and organs within a subject's body. In CT imaging systems a detector array, including a series of detector elements or sensors, produces similar signals through various positions as a gantry is displaced around a subject or object being imaged, allowing volumetric image reconstructions to be obtained.

A CT imaging system may include an annular scan window disposed within an interior wall of the gantry formed within an opening or a bore of the gantry. The scan window is made of an X-ray transparent material that enables X-rays emitted from an X-ray source to pass through an object or subject being imaged for detection by a detector. Typically, two ends of a sheet made of the X-ray transparent material are joined together via joint to form a joined member. Larger scan windows are difficult to manage due to cracking, manufacturing of the joint, and contamination. Over time, the joint can crack. In addition, the joint can become contaminated during the cracking process, prior to actual mechanical failure.

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible forms of the subject matter. Indeed, the subject matter may encompass a variety of forms that may be similar to or different from the embodiments set forth below.

In one embodiment, a scan window for an imaging system is provided. The scan window includes at least one flexible sheet made of an X-ray transparent material and having a first end and a second end. The scan window also includes at least one tapered joint formed between the first end and the second end and secured via a bonding agent to form a joined member with the at least one flexible sheet.

In another embodiment, a gantry housing for an imaging system is provided. The gantry housing includes a scan window. The scan window includes at least one sheet made of an X-ray transparent material and having a first tapered end and a second tapered end. The scan window also includes at least one tapered joint formed between the first tapered end and the second tapered end and secured via a bonding agent to form a joined member with the sheet.

In a further embodiment, a joined member is provided. The joined member includes a flexible sheet made of a plastic material and having a first tapered end and a second tapered end. The flexible cylinder member also includes a tapered joint formed between the first tapered end and the second tapered end overlapping with each other and secured via a bonding agent to form the joined member.

BRIEF DESCRIPTION OF THE DRAWINGS

These and other features, aspects, and advantages of the disclosed subject matter will become better understood when the following detailed description is read with reference to the accompanying drawings in which like characters represent like parts throughout the drawings, wherein.

DETAILED DESCRIPTION

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While aspects of the following discussion may be provided in the context of medical or health care imaging, it should be appreciated that the present techniques are not limited to such medical contexts. Indeed, the provision of examples and explanations in such a medical context is only to facilitate explanation by providing instances of real-world implementations and applications. However, the present approaches may also be utilized in other contexts, such as tomographic image reconstruction for industrial CT used in non-destructive inspection of manufactured parts or goods (i.e., quality control or quality review applications), and/or the non-invasive inspection of packages, boxes, luggage, and so forth (i.e., security or screening applications). In general, the present approaches may be useful in any imaging or screening context utilizing a generally annular or cylindrical scan window.

The present disclosure provides embodiments for an annular or cylindrical scan window. In particular, the annular or cylindrical scan window is disposed in a gantry of an imaging system (e.g., CT imaging system). In certain embodiments, the annular or cylindrical scan window includes at least one sheet having ends joined by an engineered joint. For example, the annular or cylindrical scan window includes at least one sheet having the ends (e.g., tapered ends) joined (e.g., fastened, bonded or secured) together via a bonding agent to form a tapered joint. The tapered ends overlap with each other to form the tapered joint. The forming of the tapered joint enables the at least one sheet to form the annular or cylindrical shape. In certain embodiments, more than one sheet may be joined together via tapered joints to form the annular or cylindrical scan window. The tapered ends at the beginning of the taper each include a thickness that is at least half a thickness of the sheet outside the tapered joint, thus, increasing the strength of the joint where the ends of the sheet are joined and extending the life of the scan window. The tapered joint is tapered over a distance that is 5 to 20 times the thickness of the sheet, thus, spreading out stresses as the annular or cylindrical scan window is being flexed (e.g., during removal or insertion into the gantry) compared to other joint configurations. The disclosed embodiments provide longer flexing life and less contamination risk for the annular or cylindrical scan window. In addition, the disclosed embodiments enable manufacturing of the scan window from commonly available plastic materials (e.g., thermoplastic polymers, polycarbonates). Further, the disclosed embodiments may also be utilized outside of medical or imaging contexts to form flexible joined members with an engineered joint.

Figure 1:
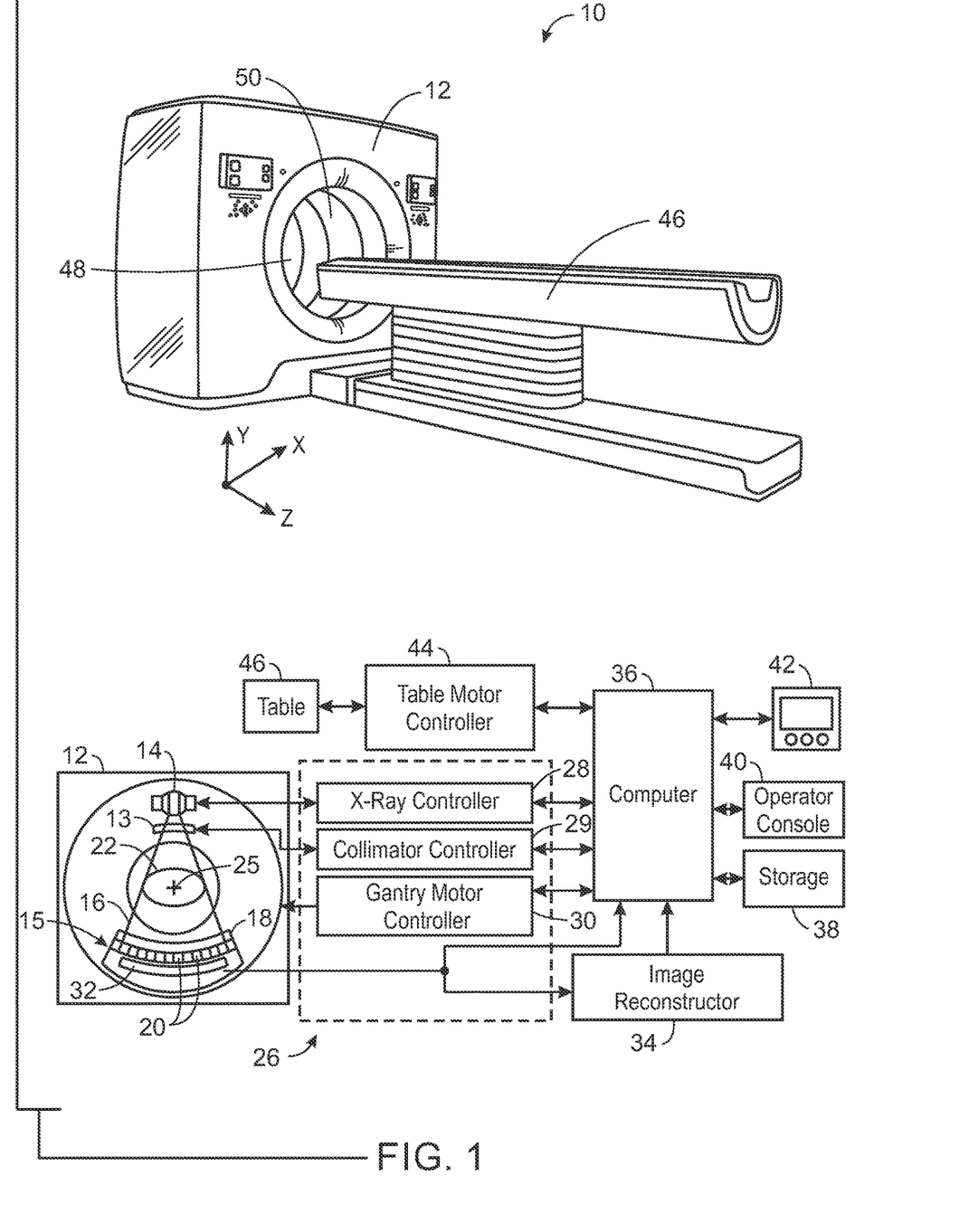
FIG. 1 is a combined pictorial view and block diagram of a computed tomography (CT) imaging system as discussed herein.

With the preceding in mind and referring to FIG. 1, a computed tomography (CT) imaging system 10 is shown, by way of example. The CT imaging system includes a gantry 12. The gantry 12 has an X-ray source 14 that projects a beam of X-rays 16 toward a detector assembly 15 on the opposite side of the gantry 12. The X-ray source 14 projects the beam of X-rays 16 through a pre-patient collimator assembly 13 that determines the size and shape of the beam of X-rays 16. The detector assembly 15 includes a collimator assembly 18 (a post-patient collimator assembly), a plurality of detector modules 20 (e.g., detector elements or sensors), and data acquisition systems (DAS) 32. The plurality of detector modules 20 detect the projected X-rays that pass through a subject or object 22 being imaged, and DAS 32 converts the data into digital signals for subsequent processing. Each detector module 20 in a conventional system produces an analog electrical signal that represents the intensity of an incident X-ray beam and hence the attenuated beam as it passes through the subject or object 22. During a scan to acquire X-ray projection data, gantry 12 and the components mounted thereon rotate about a center of rotation 25 (e.g., isocenter) so as to collect attenuation data from a plurality of view angles relative to the imaged volume.

Rotation of gantry 12 and the operation of X-ray source 14 are governed by a control system 26 of CT imaging system 10. Control system 26 includes an X-ray controller 28 that provides power and timing signals to an X-ray source 14, a collimator controller 29 that controls a length and a width of an aperture of the pre-patient collimator 13 (and, thus, the size and shape of the beam of X-rays 16), and a gantry motor controller 30 that controls the rotational speed and position of gantry 12. An image reconstructor 34 receives sampled and digitized X-ray data from DAS 32 and performs high-speed image reconstruction. The reconstructed image is applied as an input to a computer 36, which stores the image in a storage device 38. Computer 36 also receives commands and scanning parameters from an operator via console 40. An associated display 42 allows the operator to observe the reconstructed image and other data from computer 36. The operator supplied commands and parameters are used by computer 36 to provide control signals and information to DAS 32, X-ray controller 28, collimator controller 29, and gantry motor controller 30. In addition, computer 36 operates a table motor controller 44, which controls a motorized table 46 to position subject 22 and gantry 12. Particularly, table 46 moves portions of subject 22 through a gantry opening or bore 48.

Figure 2:
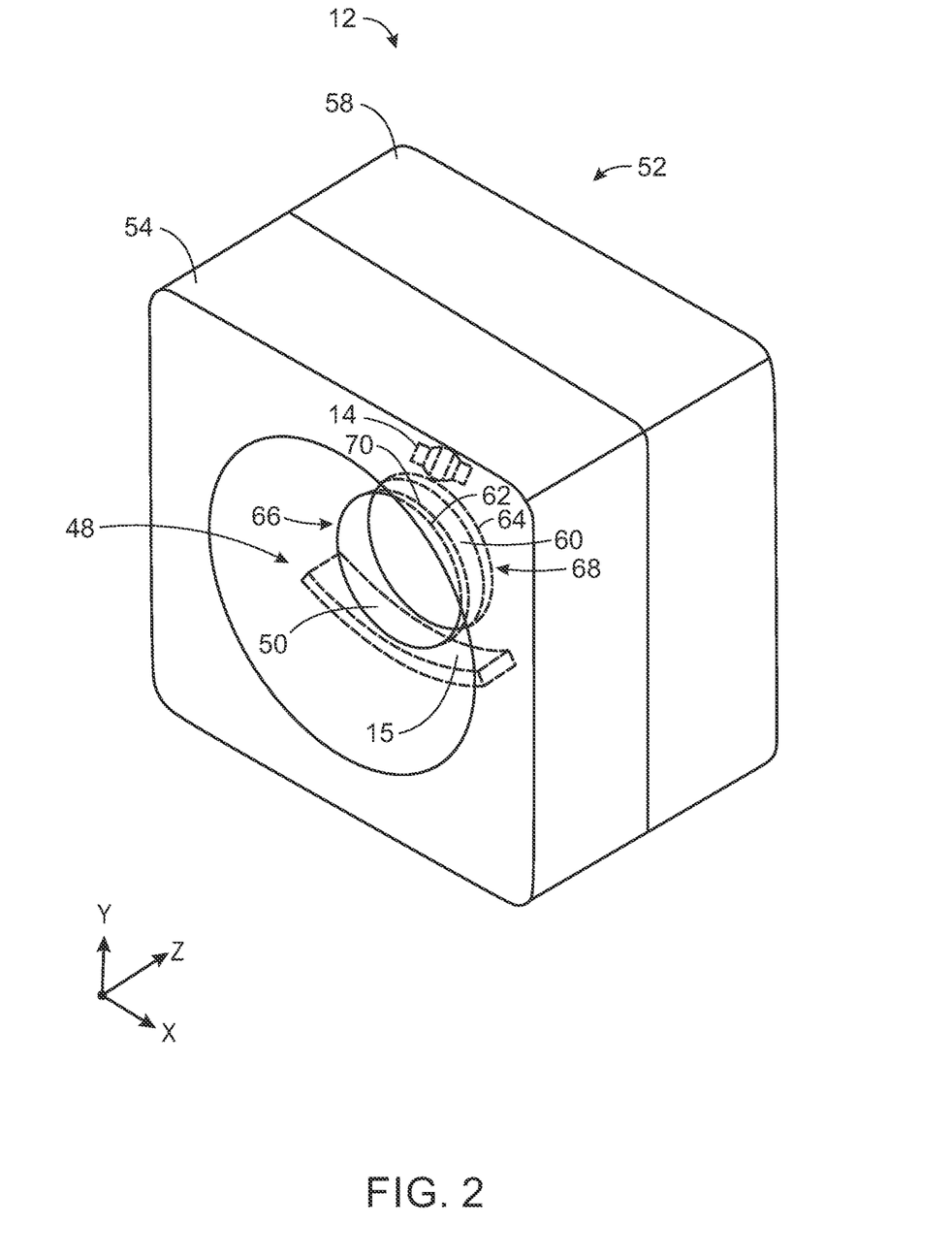
FIG. 2 is a perspective view of a gantry having an opening or bore extending therethrough, in accordance with aspects of the present disclosure.

FIG. 2 is a perspective view of the gantry 12 having an opening or bore 48 extending through the gantry 12. Although the following embodiments are discussed in terms of the CT imaging system, the embodiments may also be utilized with other imaging systems (e.g., positron emission tomography (PET) imaging system, CT/PET imaging system, single photon emission computed tomography (SPECT) imaging system, and other hybrid CT imaging systems, etc.) that include a scan window 50. The gantry 12 includes a housing 52, the gantry 12 includes a stationary section and a rotating section. The rotating section rotates around an axis which lies in the z-direction (which corresponds to a body-axis direction) relative to the stationary section. The X-ray source 14 and the detector assembly 15 are rotating elements of the rotating section. The housing 52 is constructed to cover the components disposed in the inside of the gantry 12. Moreover, the housing 52 forms space for movement in which the rotating section is capable of moving about the axis in the z-direction in the space surrounded by the housing 52.

As depicted, the housing 52 includes a front cover 54 and a rear cover 58. In another exemplary embodiment, the housing 52 may include a main cover (not shown) positioned between the front cover 54 and the rear cover 58. The front cover 54 is fixed on the side of a front surface of the gantry 12, while the rear cover 58 is fixed on the side of a back surface of the gantry 12. The front cover 54 and a rear cover 58 are stationary. The number and structure of covers forming the housing 52 may differ from those depicted in FIG. 2.

Within the bore 48, a gap may be formed between the front cover 54 and the rear cover 58. The scan window 50 is constructed so as to be fitted between the front cover 54 and the rear cover 58 to fill the gap. A worker (e.g., field engineer or employee in a manufacturing facility of an imaging system) can manually fit the scan window 50 within the bore 48 to fill the gap. The worker can also manually remove the scan window 50 from the bore 48. The scan window 50 can be inserted or removed from the bore 48 flexing a portion of the scan window 50 inward to partially fold or deform the scan window 50. The flexibility of the material used in the scan window 50 allows it to be installed or removed while the front cover 54 and rear cover 58 remain in place.

During an imaging session, a subject or patient is moved within the bore 48. The scan window 50 self-supports and acts as a safety barrier to keep the subject or patient from contacting rotating components within the gantry 12.

The scan window 50 includes a main body 60 and end members 62, 64 (e.g., elastic members, flexible members, gaskets, etc.). The end members 62, 64 are disposed on an outer surface of the main body 60 at ends 66, 68, respectively. The ends 66, 68 are located adjacent to the front cover 54 and the rear cover 58. The scan window 50 has a cylindrical or annular shape. The scan window 50 is open at both ends 66, 68.

The main body 60 is formed of a single sheet 70 made of a plastic material that is transparent to X-rays (e.g., having minimal attenuation) and is flexible or deformable. For example, the plastic material may be a thermoplastic polymer or a polycarbonate. The single sheet 70 may be made of another type of plastic material that is also transparent to X-rays and flexible or deformable.

As described in greater detail below, ends (e.g., tapered ends) of the single sheet 70 are joined together via an engineered joint (e.g., a tapered joint) to form the cylindrical or annular shape. A length (e.g., width) of the engineered joint (e.g., in a direction perpendicular to a central axis of the scan window 50) is approximately 5 to 20 times the thickness of the sheet 70. In certain embodiments, the length (e.g., width) of the joint is approximately 10 times the thickness of the sheet 70. The tapering of the joint spreads out the stresses as the joint is flexed.

The ends of single sheet 70 are secured together to form the engineered joint via a bonding agent. In certain embodiments, the bonding agent may be plastic-dissolving, UV-cured, or epoxy-based bonding agent. The bonding agent is utilized to fill in all potential empty volume in the engineered joint to provide continuous flow of the stresses through the joint during operation and flexing.

In certain embodiments, the scan window 50 may be formed of multiple sheets 70 joined together via multiple engineered joints (e.g., tapered joints). For example, an end (e.g., tapered end) of one sheet 70 may be secured to an end (e.g., tapered end) of another sheet 70 to form the engineered joint.

The engineered joint has the strength capability of the base material of the sheet 70. The engineered joint has an increased life of at least 3 to 4 times the life of a typical joint used to form the main body 60 of the scan window 50. The engineered joint may improve the IFR90 (infantile failure rate in the first 90 days) of the scan window 50. The engineered joint may also improve the long-term reliability of the scan window 50 over a period of years. The engineered joint may be especially useful for large cover scanners (70 centimeters (cm) and above). Due to the reduced cracking risk compared with other joints, the engineered joint will receive less contaminants over time (which is a problem for larger scan windows with lots of surface area). The engineered joint also reduces downtime for the imaging system due to the longer window service life with flexing. In addition, the engineered joint enables simpler cleaning of the scan window 50 since it takes longer for the scan window 50 to crack. Further, the engineered joint maintains a more robust physical barrier between the subject or patient being scanned and internal parts of the gantry 12.

Figure 3:
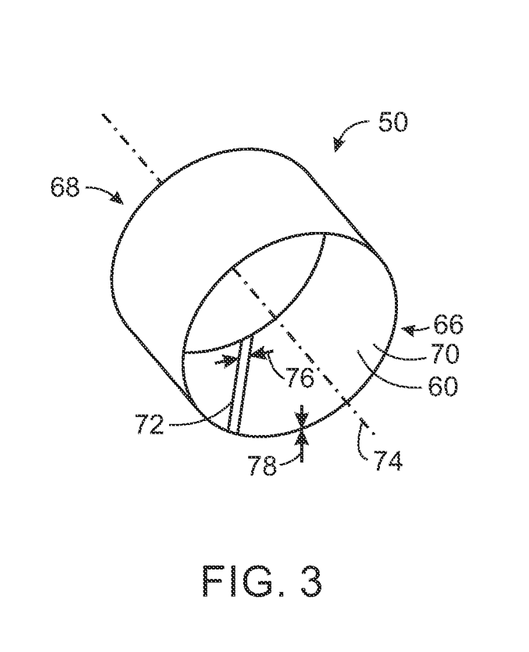
FIG. 3 is a perspective view of a main body of a joined member (e.g., having an angled joint), in accordance with aspects of the present disclosure.
Figure 4:
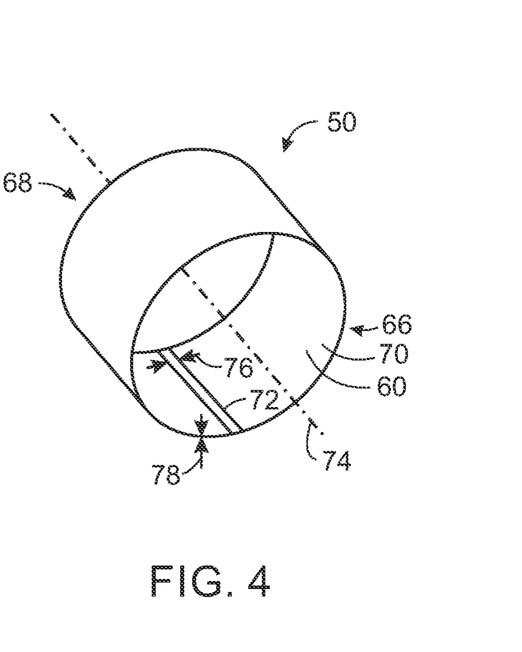
FIG. 4 is a perspective view of a main body of a joined member (e.g., having a parallel joint), in accordance with aspects of the present disclosure.

FIG. 3 is a perspective view of a main body 60 of a joined member 50, such as a scan window, having an angled joint. The main body 60 includes ends (e.g., tapered ends) of a single sheet 70 joined together to form an engineered joint 72 (e.g., tapered joint). The tapered joint 72 extends from the end 66 to the end 68. As depicted, the tapered joint 72 is angled (i.e., non-parallel) relative to a central axis 74. In certain embodiments (see FIG. 4), the tapered joint 72 is parallel with the central axis 74. FIG. 4 is a perspective view of a main body 60 of a joined member 50, such as a scan window, having a joint 72 that is parallel with the central axis 74. A length 76 (e.g., width) of the tapered joint 72 (e.g., in a direction perpendicular to the central axis 74 of the scan window 50) is approximately 5 to 20 times a length 78 (e.g., thickness) of the sheet 70. In certain embodiments, the width 76 of the joint is approximately 10 times the thickness 78 of the sheet 70. The tapering of the joint 72 spreads out the stresses as the tapered joint 72 is flexed.

Figure 5:
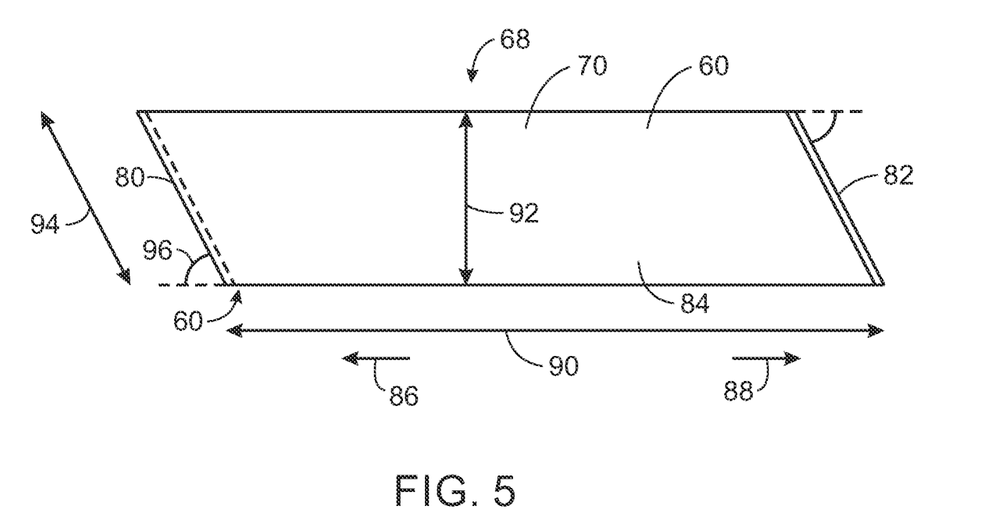
FIG. 5 is a top view of a sheet for forming the main body of the joined member in FIG. 3, in accordance with aspects of the present disclosure.
Figure 6:
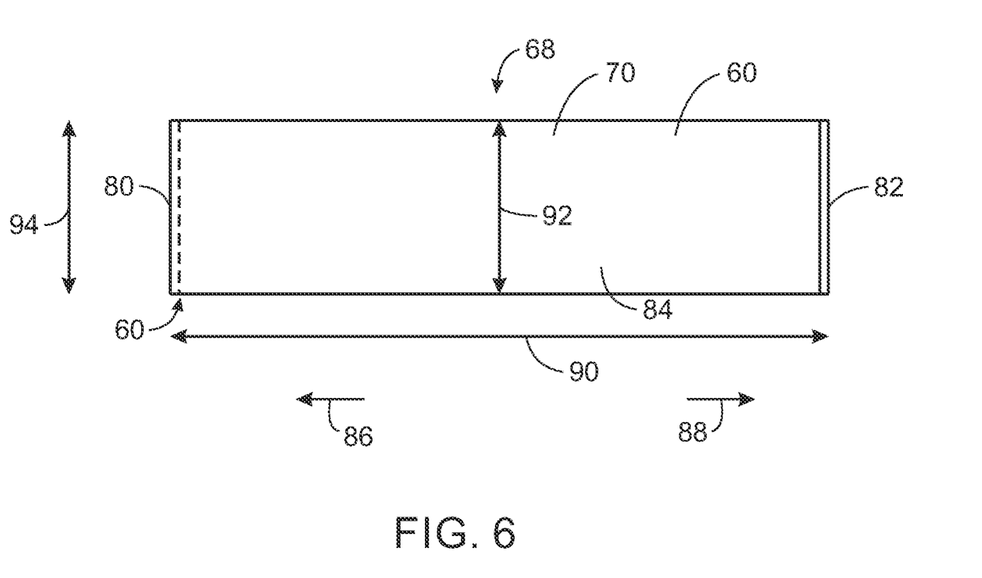
FIG. 6 is a top view of a sheet for forming the main body of the joined member in FIG. 4, in accordance with aspects of the present disclosure.

FIGS. 5 and 6 are top views of the sheets 70 for forming the respective main bodies 60 of the joined members 50, such as scan windows in FIGS. 3 and 4. The sheet 70 includes ends 80, 82 (e.g., longitudinal ends) flanking a central portion 84 of the sheet 70. Each end 80, 82 is a tapered end. The ends 80, 82 are joined together to form a tapered joint that is secured via a bonding agent. The ends 80, 82 overlap to form the tapered joint. The end 80 tapers in a direction 86 (e.g., oriented from the end 82 to the end 80). The end 82 tapers in a direction 88 (e.g., oriented from the end 80 to the end 82). In certain embodiments, the ends 80, 82 continuously taper. In certain embodiments, the ends 80, 82 initially taper and then maintain a constant thickness toward a most distal location of the ends 80, 82.

The sheet 70 has a length 90 (e.g., longitudinal length) and a length 92 (e.g., width) (in the central portion 84 and perpendicular to the length 90). The length 90 is greater than the length 92 (e.g., width). In FIG. 5, a length 94 of the ends 80, 82 is greater than the length 92 (e.g., width) of the central portion 84 of the sheet 70. In FIG. 6, the length 94 of the ends 80, 82 is the same as the length 92 (e.g., width) of the central portion 84 of the sheet 70. In FIG. 5, the ends 80, 82 are angled relative to the length 90. In certain embodiments, an angle 96 formed between the ends 80, 82 and the length 92 (e.g., width) may be approximately 60 degrees. In certain embodiments, the angle 96 may range from approximately 90 degrees (as depicted in FIG. 6) to approximately 30 degrees. The length 90 of the sheet 70 is approximately equal to the circumference of the bore 48. In an exemplary embodiment, the design of the joined member or scan window 50 is best suited for sheet lengths 90 greater than approximately 6 inches with no upper limit. A flexible, short scan window of less than 6 inches in length can often self-support and may not need this type of engineered joint. However, as the sheet lengths increase, the need for this type of engineered joint is more critical.

The sheet 70 is made of a plastic material that is transparent to X-rays (e.g., having minimal attenuation) and is flexible or deformable. For example, the plastic material may be a thermoplastic polymer or polycarbonate. The single sheet 70 may be made of another plastic material that is also transparent to X-rays and deformable. In certain embodiments, where a flexible cylindrical member is made utilizing a tapered joint for non-imaging applications, the sheet 70 made of a plastic material that is flexible or deformable (without having to take into account the material's transparency to X-rays) and has the desired material strength for the purpose of the flexible cylindrical member.

Figure 7:
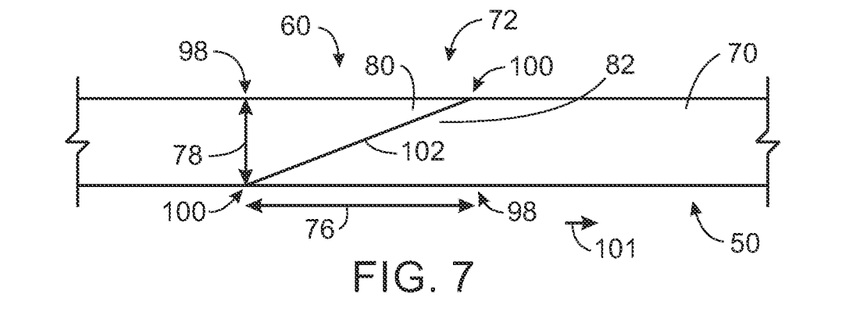
FIG. 7 is an end view of a portion of a main body of a joined member having a tapered joint (e.g., having a full ramp on both sides), in accordance with aspects of the present disclosure.

FIG. 7 is an end view of a portion of the main body 60 of a joined member 50, such as a scan window having a tapered joint 72 (e.g., having a full ramp on both sides). A sheet 70 has ends 80, 82 that overlap to form the tapered joint 72. More specifically, the ends 80, 82 taper and overlap with each other to form the tapered joint 72. Each tapered end 80, 82 has a full ramp. In other words (as shown with respect to tapered end 80), each tapered end 80, 82 decreases (80) or increases (with respect to tapered end 82) in thickness 78 from a beginning location 98 (e.g., upstream location) of the taper to an ending location 100 (e.g., downstream location) at the most distal location of the ends 80, 82. As depicted in FIG. 7, each tapered end 80, 82 continuously decreases or narrows in thickness 78 along the length 76 of the tapered joint 72 from the beginning location 98 to the ending location 100 at the most distal location of the ends 80, 82. The most distal location of the tapered ends 80, 82 forms a mating point. The thickness 78 of the tapered ends 80, 82 at the beginning of the taper is approximately the same as the thickness 78 of the sheet 70 in a location outside of the tapered joint 72. In certain embodiments, the thickness 78 may be approximately 1.5 millimeters (mm) (±0.05 mm) or less. In certain embodiments, the thickness 78 may be approximately 1.0 mm (±0.05 mm) or less. Utilization of the tapered joint 72 enables the thickness 78 of the sheet 70 to be less than 1.0 mm (±0.05 mm). In addition, the thickness 78 at the beginning location 98 of the taper will cause it to take longer for a crack to develop and progress under flexion of the main body 60 compared to other types of joints.

The length 76 (e.g., width) of the tapered joint 72 (e.g., in a direction perpendicular to the central axis 74 of the scan window 50 is approximately 5 to 20 times a length 78 (e.g., thickness) of the sheet 70. In certain embodiments, the length 76 (e.g., width) of the joint 72 (e.g., in a direction 101, which is perpendicular to the central axis of the scan window 50) is approximately 10 times the thickness 78 of the sheet 70. The tapering of the joint 72 spreads out the stresses as the tapered joint 72 is flexed.

Bonding agent is disposed along an interface 102 between the tapered ends 80, 82. Due to the bonding agent, the thickness 78 of the main body 60 in the region along the tapered joint 72 may be greater than the thickness 78 of the sheet 70 at a location outside the tapered joint 72. An interior surface of the main body 60 at location 100 may be polished to remove excess bonding agent, while on exterior surface of the main body 60 at location 100 any excess bonding agent may remain.

Figure 8:
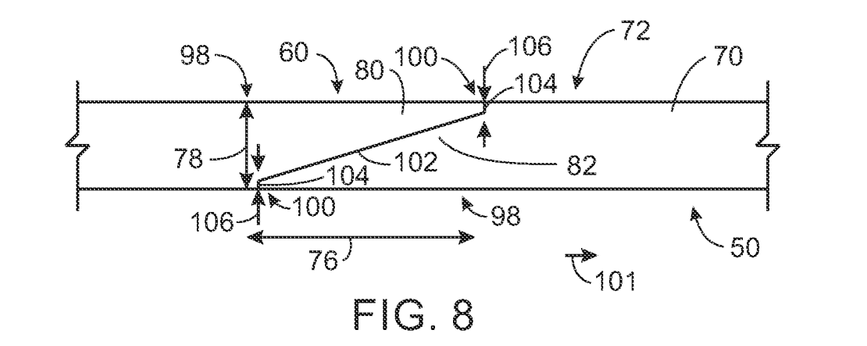
FIG. 8 is an end view of a portion of a main body of a joined member having a tapered joint (e.g., having a step on both sides), in accordance with aspects of the present disclosure.

FIG. 8 is an end view of a portion of a main body 60 of a joined member 50, such as a scan window having a tapered joint 72 (e.g., having steps on both sides). A sheet 70 has ends 80, 82 that overlap to form the tapered joint 72. More specifically, the ends 80, 82 taper and overlap with each other to form the tapered joint 72. Each tapered end 80, 82 has a partial ramp that ends in a step 104 (e.g., mating step). In other words, each tapered end 80, 82 decreases in thickness 78 from a beginning location 98 (e.g., upstream location) of the taper to an ending location 100 (e.g., downstream location) at the most distal location of the ends 80, 82. As depicted in FIG. 8, each tapered end 80, 82 continuously decreases or narrows in the thickness 78 along the length 76 of the tapered joint 72 from the beginning location 98 to the step 104. The step 104 has a length 106 (e.g., thickness) of approximately 0.25 mm (±0.05 mm). The thickness 78 of the tapered ends 80, 82 at the beginning of the taper is approximately the same as the thickness 78 of the sheet in a location outside of the tapered joint 72. In certain embodiments, the thickness 78 may be approximately 1.5 millimeters (mm) (±0.05 mm) or less. In certain embodiments, the thickness 78 may be approximately 1.0 mm (±0.05 mm) or less. Utilization of the tapered joint 72 enables the thickness 78 of the sheet 70 to be less than 1.0 mm (±0.05 mm). In addition, the thickness 78 at the beginning location 98 of the taper will cause it to take longer for a crack to develop and progress under flexion of the main body 60 compared to other types of joints.

The length 76 (e.g., width) of the tapered joint 72 (e.g., in a direction perpendicular to the central axis 74 of the scan window 50) is approximately 5 to 20 times a length 78 (e.g., thickness) of the sheet 70. In certain embodiments, the length 76 (e.g., width) of the joint is approximately 10 times the thickness 78 of the sheet 70. The tapering of the joint 72 spreads out the stresses as the tapered joint 72 is flexed.

Bonding agent is disposed along the interface 102 between the tapered ends 80, 82. Due to the bonding agent, the thickness 78 of the main body 60 in the region along the tapered joint 72 may be greater than the thickness 78 of the sheet 70 at a location outside the tapered joint 72. An interior surface of the main body 60 at location 100 may be polished to remove excess bonding agent, while on exterior surface of the main body 60 at location 100 any excess bonding agent may remain.

Figure 9:
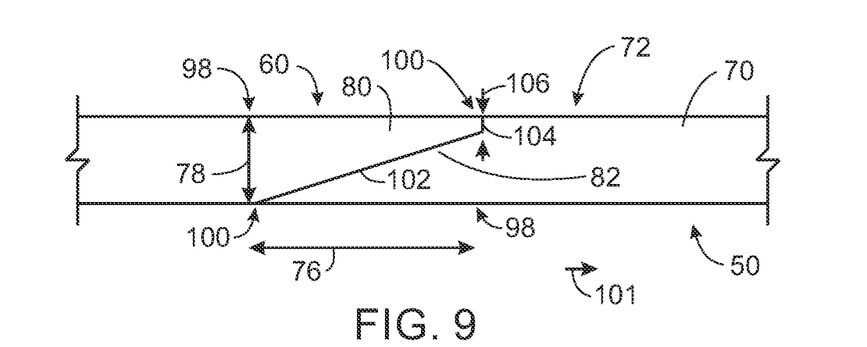
FIG. 9 is an end view of a portion of a main body of a joined member having a tapered joint (e.g., having a full ramp on one side and a step on one side), in accordance with aspects of the present disclosure.

FIG. 9 is an end view of a portion of a main body 60 of a joined member 50, such as a scan window having a tapered joint 72 (e.g., having a full ramp on one side and a step on one side). A sheet 70 has ends 80, 82 that overlap to form the tapered joint 72. More specifically, the ends 80, 82 taper and overlap with each other to form the tapered joint 72. One tapered end 80 has a full ramp that ends in a mating point. The other tapered end 82 has a partial ramp that ends in the step 104 (e.g., mating step 104). In other words, each tapered end 80, 82 decreases in thickness 78 from a beginning location 98 (e.g., upstream location) of the taper to an ending location 100 (e.g., downstream location) at the most distal location of the ends 80, 82. As depicted in FIG. 9, the tapered end 80 continuously decreases or narrows in the thickness 78 along the length 76 of the tapered joint 72 from the beginning location 98 to the step 104. The tapered end 82 continuously decreases or narrows in thickness 78 along the length 76 (e.g., width) of the tapered joint 72 from the beginning location 98 to the mating point. The step 104 has a length 106 (e.g., thickness) of approximately 0.25 mm (±0.05 mm). The thickness 78 of the tapered ends 80, 82 at the beginning of the taper is approximately the same as the thickness 78 of the sheet 70 in a location outside of the tapered joint 72. In certain embodiments, the thickness 78 may be approximately 1.5 millimeters (mm) (±0.05 mm) or less. In certain embodiments, the thickness 78 may be approximately 1.0 mm (±0.05 mm) or less. Utilization of the tapered joint 72 enables the thickness 78 of the sheet 70 to be less than 1.0 mm (±0.05 mm). In addition, the thickness 78 at the beginning location 98 of the taper will cause it to take longer for a crack to develop and progress under flexion of the main body 60 compared to other types of joints.

The length 76 (e.g., width) of the tapered joint 72 (e.g., in a direction perpendicular to the central axis 74 of the scan window 50) is approximately 5 to 20 times a length 78 (e.g., thickness) of the sheet 70. In certain embodiments, the length 76 (e.g., width) of the joint is approximately 10 times the thickness 78 of the sheet 70. The tapering of the joint 72 spreads out the stresses as the tapered joint 72 is flexed.

Bonding agent is disposed along the interface 102 between the tapered ends 80, 82. Due to the bonding agent, the thickness 78 of the main body 60 in the region along the tapered joint 72 may be greater than the thickness 78 of the sheet 70 at a location outside the tapered joint 72. An interior surface of the main body 60 at location 100 may be polished to remove excess bonding agent, while on exterior surface of the main body 60 at location 100 any excess bonding agent may remain.

Figure 10:
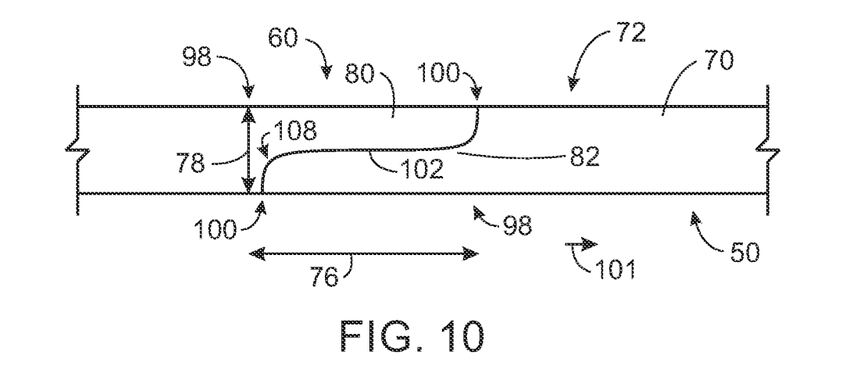
FIG. 10 is an end view of a portion of a main body of a joined member having a tapered joint (e.g., having mating radii on both sides), in accordance with aspects of the present disclosure.

FIG. 10 is an end view of a portion of a main body 60 of a joined member 50, such as a scan window having a tapered joint 72 (e.g., having mating radii on both sides). A sheet 70 has ends 80, 82 that may be joined together or overlap to form the tapered joint 72. More specifically, the ends 80, 82 taper and overlap with each other to form the tapered joint 72. Each tapered end 80, 82 ends in a radius 108 (e.g., rounded edge) that narrows in the thickness 78. In particular, each tapered end 80, 82 initially decreases in thickness 78 from at a beginning location 98 (e.g., upstream location) of the taper. Then each tapered end 80, 82 has approximately a constant thickness 78 up until the radius 108. Each tapered end 80, 82 beginning at the radius 108 continuously decreases in thickness 78 until an ending location 100 (e.g., downstream location) at the most distal location of the ends 80, 82. The thickness 78 of the tapered ends 80, 82 at the beginning of the taper is approximately the same as the thickness 78 of the sheet 70 in a location outside of the tapered joint 72. In certain embodiments, the thickness 78 may be approximately 1.5 millimeters (mm) (±0.05 mm) or less. In certain embodiments, the thickness 78 may be approximately 1.0 mm (±0.05 mm) or less. Utilization of the tapered joint 72 enables the thickness 78 of the sheet 70 to be less than 1.0 mm (±0.05 mm). In addition, the thickness 78 at the beginning location 98 of the taper will cause it to take longer for a crack to develop and progress under flexion of the main body 60 compared to other types of joints.

The length 76 (e.g., width) of the tapered joint 72 (e.g., in a direction perpendicular to the central axis 74 of the scan window 50) is approximately 5 to 20 times a length 78 (e.g., thickness) of the sheet 70. In certain embodiments, the length 76 (e.g., width) of the joint is approximately 10 times the thickness 78 of the sheet 70. The tapering of the joint 72 spreads out the stresses as the tapered joint 72 is flexed.

Bonding agent is disposed along the interface 102 between the tapered ends 80, 82. Due to the bonding agent, the thickness 78 of the main body 60 in the region along the tapered joint 72 may be greater than the thickness 78 of the sheet 70 at a location outside the tapered joint 72. An interior surface of the main body 60 at location 100 may be polished to remove excess bonding agent, while on exterior surface of the main body 60 at location 100 any excess bonding agent may remain.

Figure 11:
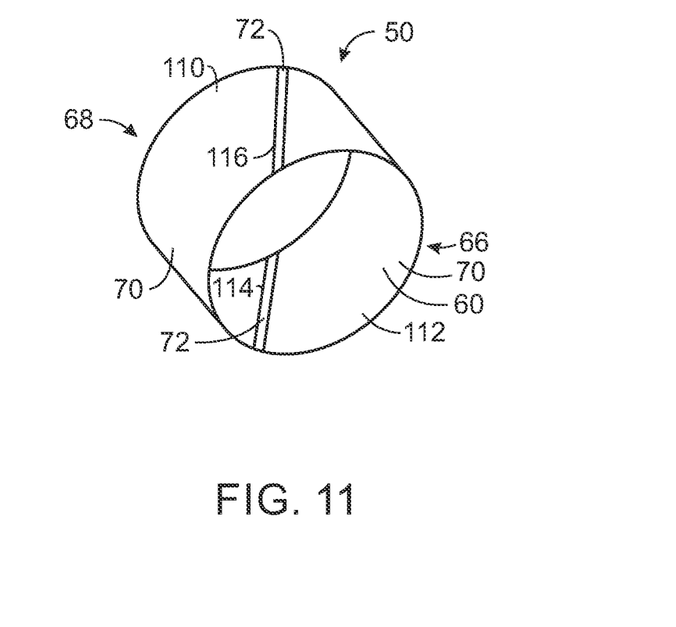
FIG. 11 is a perspective view of a main body of a joined member (e.g., formed from multiple sheets), in accordance with aspects of the present disclosure.
Figure 12:
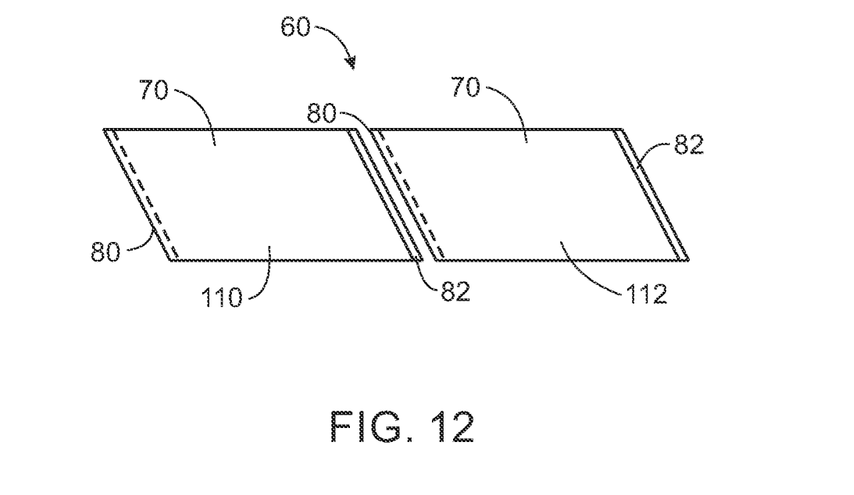
FIG. 12 is a top view of a plurality of sheets for forming the main body of the joined member in FIG. 11, in accordance with aspects of the present disclosure.

FIG. 11 is a perspective view of a main body 60 of a joined member 50, such as a scan window. The main body 60 of the joined member 50 is made of a plurality of sheets 70 (e.g., a first sheet 110 and a second sheet 112, also depicted in FIG. 12). FIG. 12 is a top view of a plurality of sheets 70 (e.g., a first sheet 110 and a second sheet 112) for forming the main body 60 of the joined member 50 in FIG. 11. As depicted in FIG. 11, the plurality of sheets 70 (e.g., a first sheet 110 and a second sheet 112) are coupled together via multiple tapered joints 72 (e.g., a first tapered joint 114 and a second tapered joint 116.) As depicted in FIGS. 11 and 12, each sheet 110, 112 has tapered ends 80, 82. End 80 of the first sheet 110 and the end 82 of the second sheet 112 are joined together (and secured via a bonding agent) to form the first tapered joint 114. End 80 of the sheet 110 and the end 82 of the second sheet 112 are jointed together (and secured via a bonding agent) to form the second tapered joint 116. The tapered joints 114, 116 may be as described above. In certain embodiments, the number of sheets 70 and tapered joints to form the joined member 50 may be greater than two.

Figure 13:
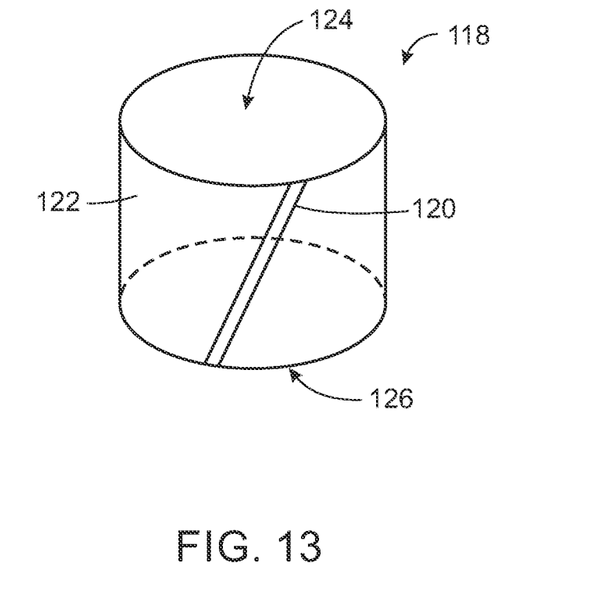
FIG. 13 is a perspective view of a cylindrical member, in accordance with aspects of the present disclosure.

As noted above, the tapered joint may be utilized with any flexible member having a cylindrical shape. For example, FIG. 13 depicts a cylindrical member 118 having a tapered joint 120. The cylindrical member 118 includes a side wall 122 made of a flexible material. The cylindrical shape of the side wall 122 is formed by the joining of the ends of a sheet 122 and securing of the ends with bonding agent to form the tapered joint 120. The tapered joint 120 may be as described above. The flexible material of the side wall 122 may be made of any plastic material having the desired flexibility and material strength to enable the cylindrical member 118 to be utilized as desired. The cylindrical member 118 includes a first end 124 and a second end 126. One or both ends 124, 126 of the cylindrical member 118 may be open or closed.

Technical effects of the disclosed embodiments include forming a main body of a scan window by coupling ends of a sheet together to form an engineered joint (e.g., tapered joint). The engineered joint has the strength capability of the base material of the sheet. The engineered joint has an increased life of at least 3 to 4 times the life of a typical joint used to form the main body of the scan window. The engineered joint may improve the IFR90 of the scan window. The engineered joint may also improve the long term reliability of the scan window over a period of years. Due to the reduced cracking risk compared with other joints, the engineered joint will receive less contaminants over time (which is a problem for larger scan windows with lots of surface area). The engineered joint also reduces downtime for the imaging system due to the longer window service life with flexing. In addition, the engineered joint enables simpler cleaning of the scan window since it takes longer for the scan window to crack. Further, the housing and scan window maintains a more robust physical barrier between the patient and internal parts of the gantry.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

This written description uses examples to disclose the present subject matter, including the best mode, and also to enable any person skilled in the art to practice the subject matter, including making and using any devices or systems and performing any incorporated methods. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A scan window for an imaging system, comprising:
at least one flexible sheet made of an X-ray transparent material and having a first end, a second end, and a length extending between the first end and the second end, wherein the first end and the second end are angled relative to the length; and
at least one tapered joint formed between the first end and the second end and secured via a bonding agent to form a joined member with the at least one flexible sheet.

2. The scan window of claim 1, wherein the first end and the second end comprise a first tapered end and a second tapered end, respectively, that overlap with each other to form the at least one tapered joint.

3. The scan window of claim 2, wherein each of the first end and the second end of the at least one flexible sheet continuously narrows from a beginning of the respective end to a most distal location of the respective end.

4. The scan window of claim 3, wherein the most distal location of at least one of the first end and the second end has a mating step.

5. The scan window of claim 3, wherein the most distal location of both the first end and the second end has the mating step.

6. The scan window of claim 3, wherein the most distal location of at least one of the first end and the second end has a mating point.

7. The scan window of claim 3, wherein the most distal location of both the first end and the second end has the mating point.

8. The scan window of claim 3, wherein the most distal location of the first end has a mating step and the most distal location of the second end has a mating point.

9. The scan window of claim 2, wherein each of the first end and the second end of the at least one flexible sheet narrows at a beginning of the respective end, then has a constant thickness until near a most distal location of the respective end before continuously narrowing to the most distal location.

10. The scan window of claim 9, wherein the most distal location of both the first end and the second end is rounded.

11. The scan window of claim 2, wherein a beginning of a taper of both the first tapered end and the second tapered end has a respective thickness that is at least half a thickness of the at least one flexible sheet at a location outside of the at least one tapered joint.

12. The scan window of claim 11, wherein the beginning of the taper of both the first tapered end and the second tapered has a respective thickness that is approximately the same as the thickness of the at least one flexible sheet at the location outside of the at least one tapered joint.

13. The scan window of claim 1, wherein the imaging system comprises a computed tomography imaging system.

14. The scan window of claim 1, wherein the at least one tapered joint is parallel with a central axis of the scan window.

15. The scan window of claim 1, wherein the at least one tapered joint is non-parallel with a central axis of the scan window.

16. The scan window of claim 1, wherein a ratio of a respective length of both the first end and the second end in a direction perpendicular to a central axis of the scan window relative to a thickness of the at least one flexible sheet ranges from 5:1 to 20:1.

17. The scan window of claim 16, wherein the ratio is 10:1.

* * * * *